(12) United States Patent
Glaser (10) Patent No.: US 11,357,642 B2
(45) Date of Patent: Jun. 14, 2022

(54) SPINAL IMPLANT SYSTEM AND METHOD (71) Applicant: Warsaw Orthopedic, Inc., Warsaw, IN (US)

(72) Inventor: Adam Glaser, Germantown, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 4 days.

(21) Appl. No.: 16/869,709

(22) Filed: May 8, 2020

(65) Prior Publication Data
US 2021/0346175 A1  Nov. 11, 2021

(51) Int. Cl.
A61B 17/70 (2006.01)
A61F 2/44 (2006.01)
A61F 2/46 (2006.01)

(52) U.S. Cl.
CPC ........ *A61F 2/4611* (2013.01); *A61B 17/7064* (2013.01); *A61F 2/4405* (2013.01)

(58) Field of Classification Search
CPC ...... A61F 2/4611; A61F 2/4405; A61F 2/442; A61F 2/4455; A61F 2/4425; A61F 2002/2839; A61F 2002/4627; A61F 2002/4632; A61B 17/7082; A61B 17/8886; A61B 17/86; A61B 17/7035; A61B 17/7032; A61B 17/8888; A61B 17/7091; A61B 17/8894; A61B 17/8877; A61B 17/7064; A61B 17/1757; A61B 34/20; A61B 34/30; A61B 34/25; A61B 2034/2051; A61B 2034/2055; A61B 2034/102; A61B 2034/107; A61B 2034/2072; A61B 2034/254; A61B 90/39; A61B 2090/037; A61B 2090/3966; A61B 2090/3762

USPC .......................................................... 606/247
See application file for complete search history.

(56) References Cited

U.S. PATENT DOCUMENTS

| 5,098,434 A | 3/1992 | Serbousek |
| 5,259,398 A | 11/1993 | Vrespa |
| 6,542,747 B1 | 4/2003 | Marino |
| 8,048,121 B2 | 11/2011 | Mitchell et al. |
| 8,267,966 B2 | 9/2012 | McCormack et al. |
| 8,894,685 B2 | 11/2014 | Mickiewicz et al. |
| 9,039,765 B2 | 5/2015 | Trieu |
| 2003/0181912 A1 | 9/2003 | Michelson |
| 2005/0240188 A1 | 10/2005 | Chow et al. |
| 2006/0085072 A1* | 4/2006 | Funk ............... A61F 2/4657 623/17.11 |
| 2009/0312800 A1* | 12/2009 | Chin ............... A61B 17/7082 606/279 |

(Continued)

FOREIGN PATENT DOCUMENTS

| WO | 02/34120 A2 | 5/2002 |
| WO | 2014/078321 A1 | 5/2014 |

*Primary Examiner* — Nicholas J Plionis
(74) *Attorney, Agent, or Firm* — Sorell, Lenna & Schmidt, LLP (57) ABSTRACT

A spinal implant comprises a proximal member including a body having a first diameter and a head having a second diameter. The body includes an outer surface disposed for non-fixation with a superior facet of a vertebra, and the second diameter being greater than the first diameter. The spinal implant comprises a distal member having a third diameter and being configured for fixation with an inferior facet of an adjacent vertebra. Systems, surgical instruments and methods are disclosed.

18 Claims, 7 Drawing Sheets

(56) References Cited

U.S. PATENT DOCUMENTS

| | | | |
|---|---|---|---|
| 2010/0068003 A1* | 3/2010 | Wagner | B21H 3/02 |
| | | | 411/386 |
| 2010/0191291 A1 | 7/2010 | Phan et al. | |
| 2011/0213423 A1 | 9/2011 | Biedermann et al. | |
| 2011/0313466 A1 | 12/2011 | Butler et al. | |
| 2014/0031934 A1 | 1/2014 | Trieu | |
| 2015/0157377 A1 | 6/2015 | Pham et al. | |
| 2020/0222127 A1* | 7/2020 | Snyder | A61B 34/20 |

* cited by examiner

SPINAL IMPLANT SYSTEM AND METHOD

TECHNICAL FIELD

The present disclosure generally relates to medical devices for the treatment of musculoskeletal disorders, and more particularly to a spinal implant system and a method for treating vertebrae.

BACKGROUND

Spinal pathologies and disorders such as degenerative disc disease, disc herniation, spondylolisthesis, stenosis, osteoporosis, tumor, kyphosis, scoliosis and other curvature abnormalities, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, injection, mobilization, rehabilitation and exercise can be effective, however, may fail to relieve the symptoms associated with these disorders. Surgical treatment of these disorders can include the use of implants for fusion and/or fixation to provide stability to a treated region. For example, surgical treatment may employ surgical instruments and implants that are manipulated for fixation with bone to immobilize a joint. This disclosure describes an improvement over these prior technologies.

SUMMARY

In one embodiment, a spinal implant is provided. The spinal implant includes a proximal member having a body with a first diameter and a head having a second diameter. The body includes an outer surface disposed for non-fixation with a superior facet of a vertebra and the second diameter is greater than the first diameter. A distal member has a third diameter and is configured for fixation with an inferior facet of an adjacent vertebra. In some embodiments, systems, surgical instruments and methods are disclosed.

In one embodiment, a method for treating a spine is provided. The method comprises the steps of: selecting a pathway that includes a facet joint including at least a portion of a facet of a first vertebra and at least a portion of a facet of a second vertebra; creating an opening in the facets along the pathway from a posterior approach to the vertebrae, the opening including a first diameter cavity of the facet of the first vertebra and a second diameter cavity of the facet of the second vertebra, the first diameter being greater than the second diameter; and delivering an implant along the pathway such that the implant is disposed in the first diameter cavity and the second diameter cavity to draw articular surfaces of the facets into engagement.

In one embodiment, the method comprises the steps of: identifying a facet joint including at least a portion of a superior articular facet of a vertebra and at least a portion of an inferior articular facet of an adjacent vertebra; determining a selected pathway that includes the facet joint; creating an opening in the facets along the selected pathway from a posterior approach to the vertebrae, the opening including a first diameter cavity of the superior articular facet and a second diameter cavity of the inferior articular facet, the first diameter being greater than the second diameter; and delivering an implant along the selected pathway via surgical navigation, the implant including a proximal member having a body with a first diameter and a head with a second diameter that is greater than the first diameter and a distal member configured for fixation with tissue such that the proximal member is disposed in the first diameter cavity and the distal member is disposed in the second diameter cavity to draw surfaces of the articular facets into engagement.

BRIEF DESCRIPTION OF THE DRAWINGS

The present disclosure will become more readily apparent from the specific description accompanied by the following drawings, in which.

DETAILED DESCRIPTION

The exemplary embodiments of the spinal implant system and related methods of use disclosed are discussed in terms of medical devices for the treatment of musculoskeletal disorders and more particularly, in terms of a spinal implant system and a method for treating a spine. In some embodiments, the systems and methods of the present disclosure comprise medical devices including surgical instruments and implants that are employed with a surgical treatment, for example, with a cervical, thoracic, lumbar and/or sacral region of a spine. In some embodiments, the present system is employed with a method including a spinal implant, for example, a bone screw that is implanted into a facet joint such that the bone screw draws a superior articular facet and an inferior articular facet into fixation to promote fusion therebetween.

In some embodiments, the present spinal implant system and method include a spinal implant, for example, a facet screw configured for engagement with a cervical facet joint. In some embodiments, the facet screw includes a proximal member and a distal member. In some embodiments, the proximal member includes a head having a first diameter and a body having a second diameter, which is less than the first diameter. In some embodiments, the distal member includes a shaft having a diameter that is less than the diameter of the body.

In some embodiments, the present spinal implant system includes a facet screw having a proximal member, for example, a body that is smooth and engages with tissue surfaces of a pilot hole formed within one or more vertebral surfaces, for example, a superior facet. In some embodiments, the diameter of the body and a diameter of the pilot hole closely match to limit translation of the facet screw.

In some embodiments, the present spinal implant system includes a facet screw having a distal member, for example, a shaft that includes a threaded portion that engages tissue surfaces of a pilot hole formed within one or more vertebral surfaces, for example, an inferior facet. In some embodiments, the diameter of the shaft is less than the diameter of the pilot hole of the superior facet so that the shaft can pass through the superior facet into the inferior facet, and/or avoid tissue damage to the superior facet. In some embodiments, the threaded portion of the shaft engages a caudal vertebra and draws the cervical facet joint tightly into a natural position. In some embodiments, the difference in the diameter of the body and the diameter of the shaft resists and/or prevents the threaded portion from engaging a cephalad vertebra during a driving process, thereby reducing and/or preventing the cervical facet joint from separating since the threaded portion does not engage the cephalad vertebra.

In some embodiments, the present spinal implant system and method are employed with a spinal implant, for example, a stepped cervical facet screw. In some embodiments, the spinal implant includes a proximal member including a body and a head, and a distal member including a shaft. In some embodiments, the body of the proximal member is configured for non-fixation with tissue surfaces of a superior articular facet and the shaft of the distal member is configured for fixation with the tissue surfaces of an inferior articular facet. In some embodiments, the head of the proximal member is configured to engage vertebral surfaces, for example, an outer surface of a superior facet and the shaft is fixed with an inferior facet for compression capability to draw articular surfaces into engagement. In some embodiments, the head defines a hexalobe drive insert or socket. In some embodiments, the present spinal implant system and method are employed with a spinal implant, for example, a cervical facet screw having a lag configuration for facet fusion and immobilization.

In some embodiments, the present spinal implant system is employed with a method of implanting a spinal implant, for example, a cervical facet screw. In some embodiments, the method includes the step of implanting a spinal implant including defining a trajectory that is robotically guided. In some embodiments, the method includes the step of drilling a stepped pilot hole into a first cervical facet and a second cervical facet. In some embodiments, the method includes the step of inserting a proximal member of the spinal implant into the first cervical facet and into a facet joint and not into the second cervical facet. In some embodiments, the method includes the step of inserting a distal member of the spinal implant into the facet joint and into the second cervical facet. In some embodiments, the method includes the step of engaging the facet screw with a surgical driver and inserting the facet screw into the facet joint. In some embodiments, the diameter of the shaft is less than the diameter of the pilot hole of a superior facet so that the shaft does not engage a bone surface in a superior facet. In some embodiments, a length of the proximal member of the facet screw is longer than a length of a pilot hole disposed through a superior facet. In some embodiments, a length of the shaft of the facet screw is longer than a length of a pilot hole disposed through an inferior facet to ensure adequate facet screw purchase.

In some embodiments, the present spinal implant system is employed with a method of lateral anterior cervical disc fixation with a robotically guided spinal implant, for example, a cervical facet screw. In some embodiments, the method includes the steps of placing a patient in a lateral position followed by a percutaneous robotically guided implantation of one or more cervical facet screws. In some embodiments, the present spinal implant system and method comprise a surgical instrument that includes a spinal implant driver guidable through an end effector of a robotic arm for spinal implant, for example, facet screw insertion. In some embodiments, the spinal implant driver is configured to rotate within an inside diameter of a robotic arm guide without becoming disengaged therefrom.

In some embodiments, the present spinal implant system and method comprise a surgical instrument that comprises a screw driver that can be employed with spinal implants, such as facet screws and/or one or more implant supports for treating a spine. In some embodiments, the present spinal implant system and method include a surgical instrument that can easily connect and disconnect from a spinal implant. In some embodiments, the present spinal implant system and method include a surgical instrument that can be employed with an end effector of a robotic arm to facilitate implantation with the robotic arm. In some embodiments, the surgical instrument is guided through the end effector for a guide-wireless screw insertion. In some embodiments, the surgical instrument comprises a robot screw driver employed with robotic and/or navigation guidance, which may include an image guide.

In some embodiments, the present spinal implant system is employed with a method used with surgical navigation, for example, fluoroscopic or image guidance. In some embodiments, the presently disclosed system and/or method reduce operating time for a surgical procedure and reduce radiation exposure due to fluoroscope or image guidance, for example, by eliminating procedural steps and patient repositioning by implanting system components in one body position.

In some embodiments, the spinal implant system of the present disclosure may be employed to treat spinal disorders, for example, degenerative disc disease, disc herniation, osteoporosis, spondylolisthesis, stenosis, scoliosis and other curvature abnormalities, kyphosis, tumor and fractures. In some embodiments, the spinal implant system of the present disclosure may be employed with other osteal and bone related applications, including those associated with diagnostics and therapeutics. In some embodiments, the disclosed spinal implant system may be alternatively employed in a surgical treatment with a patient in a prone or supine position, and/or employ various surgical approaches to the spine, including anterior, posterior, posterior mid-line, direct lateral, postero-lateral, and/or antero-lateral approaches, and in other body regions. The spinal implant system of the present disclosure may also be alternatively employed with procedures for treating the cervical, lumbar, thoracic, sacral and pelvic regions of a spinal column. The spinal implant system of the present disclosure may also be used on animals, bone models and other non-living substrates, for example, in training, testing and demonstration.

The spinal implant system of the present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. In some embodiments, as used in the specification and including the appended claims, the term "tissue" includes soft tissue, ligaments, tendons, cartilage and/or bone unless specifically referred to otherwise.

The following discussion includes a description of a spinal implant system including a spinal implant, related components and methods of employing the spinal implant system in accordance with the principles of the present disclosure. Alternate embodiments are also disclosed. Reference is made in detail to the exemplary embodiments of the present disclosure, which are illustrated in the accompanying figures. Turning to FIGS. 1-7, there are illustrated components of a surgical system, for example, a spinal implant system 10.

The components of spinal implant system 10 can be fabricated from biologically acceptable materials suitable for medical applications, including metals, synthetic polymers, ceramics and bone material and/or their composites. For example, the components of spinal implant system 10, individually or collectively, can be fabricated from materials such as stainless steel alloys, aluminum, commercially pure titanium, titanium alloys, Grade 5 titanium, super-elastic titanium alloys, cobalt-chrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO₄ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, for example, composites of metals and calcium-based ceramics, composites of PEEK and calcium based ceramics, composites of PEEK with resorbable polymers, totally resorbable materials, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of spinal implant system 10 may have material composites, including the above materials, to achieve various desired characteristics such as strength, rigidity, elasticity, compliance, biomechanical performance, durability and radiolucency or imaging preference. The components of spinal implant system 10, individually or collectively, may also be fabricated from a heterogeneous material such as a combination of two or more of the above-described materials. The components of spinal implant system 10 may be monolithically formed, integrally connected or include fastening elements and/or instruments, as described herein.

Spinal implant system 10 is employed, for example, with a fully open surgical procedure, a minimally invasive procedure including percutaneous techniques, and mini-open surgical techniques to deliver and introduce instrumentation and/or a spinal implant at a surgical site of a patient, for example, regions of a spine including vertebrae, iliac bone and/or articular surfaces of a vertebral joint, for example, a cervical facet joint. In some embodiments, the components of spinal implant system 10 are employed to stabilize and maintain structural integrity while reducing stress on a facet joint and/or portions of the anatomy adjacent the facet joint. In some embodiments, spinal implant system 10 is configured to treat facet joint disorders including those caused by degeneration or trauma. In some embodiments, spinal implant system 10 is adapted to immobilize opposing naturally separated surfaces of a facet joint. In some embodiments, spinal implant system 10 can include one or more components of one or more spinal constructs, for example, bone fasteners, interbody devices, interbody cages, spinal rods, tethers, connectors, plates and/or bone graft, and can be employed with various surgical procedures including surgical treatment of a cervical, thoracic, lumbar and/or sacral region of a spine, and/or iliac bone.

Figure 1:
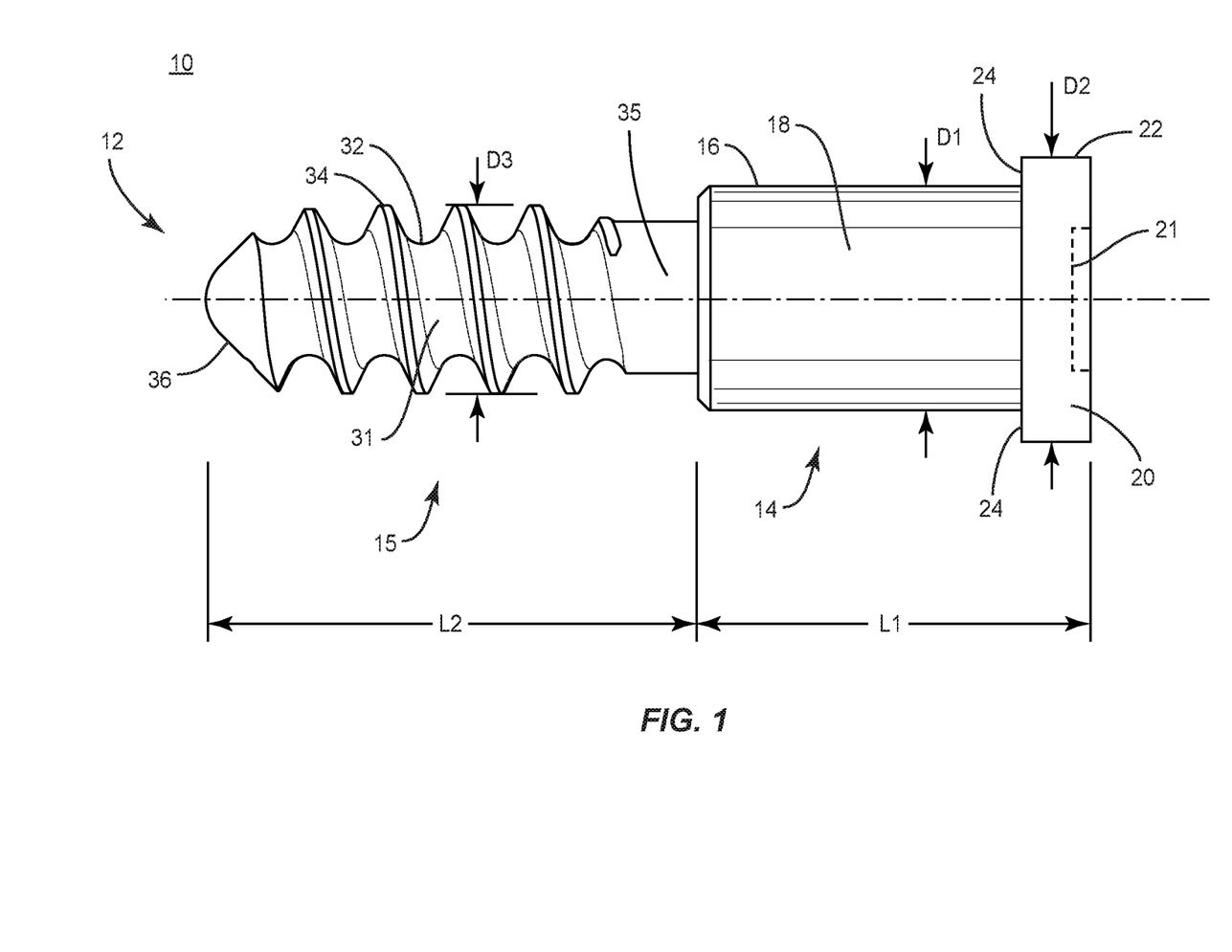
FIG. 1 is a side view of components of one embodiment of a spinal implant in accordance with the principles of the present disclosure.

Spinal implant system 10 includes a spinal implant, for example, cervical facet screw 12, as shown in FIG. 1. Facet screw 12 is configured to assist in the treatment of facet joint disorders including those caused by degeneration or trauma. For example, facet screw 12 is configured to engage both a superior facet of a cervical vertebra V1 and an inferior facet of an adjacent cervical vertebra V2 so that articular surfaces of the facets are drawn into close proximity, for example, to engage the articular surfaces, provide engagement for fixation to promote fusion therebetween and/or to place the cervical facet joint into a natural position. In some embodiments, facet screw 12 includes a stepped configuration, which may include portions of different diameters, lengths, and/or thickness that can be increasing, decreasing or alternating. In some embodiments, facet screw 12 may be uniformly tapered.

Facet screw 12 includes a proximal member 14 and a distal member 15. Proximal member 14 includes a body 16 having an outer surface 18. Surface 18 is configured for non-fixation with tissue surfaces of an opening, for example, tissue surfaces of cavity 26 formed within the superior facet of V1. Body 16 is disposable within cavity 26 such that surface 18 is configured for a non-fixed engagement with tissue surfaces that define cavity 26. In some embodiments, a non-fixed configuration of surface 18 with tissue surfaces of cavity 26 includes a non-penetrating, slidable engagement. In some embodiments, non-fixed engagement includes a range of frictional engagement between surface 18 and tissue surfaces defining cavity 26. Surface 18 includes a uniform, even surface configuration. In some embodiments, surface 18 may have various surface configurations, for example, rough, arcuate, undulating, porous, semi-porous, dimpled, polished and/or textured.

Body 16 has a diameter D1. Cavity 26 has a diameter DD1 and in some embodiments, cavity 26 is a pilot hole formed in tissue of the superior facet. Diameter D1 is sized relative to DD1 such that surface 18 has a non-fixation engagement, as described herein, with tissue surfaces of cavity 26. Proximal member 14 includes a length L1. Length L1 is greater than a length of cavity 26.

Figure 7:
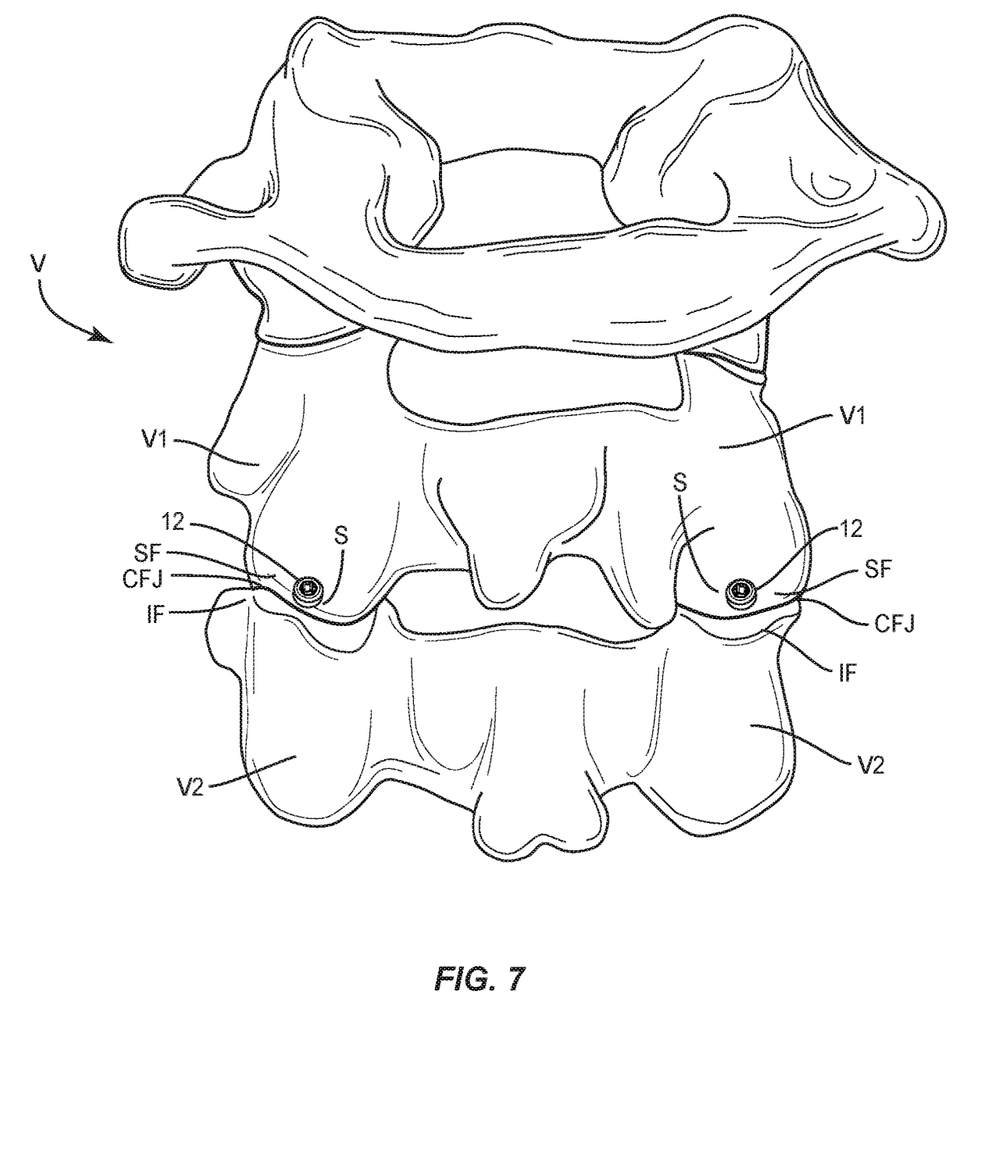
FIG. 7 is a plan view of the components and vertebrae shown in FIG. 6.

Proximal member 14 includes a head 20 having a circumferential flange 22 extending from surface 18 and being engageable with the superior facet when distal member 15 is fixed with the inferior facet to draw articular surfaces of the facets into close proximity, for example, to engage the articular surfaces, provide engagement for fixation to promote fusion therebetween and/or to place the cervical facet joint into a natural position. Flange 22 includes a planar surface 24 disposed in a substantially flush engagement with an outer surface of the superior facet, as shown in FIG. 7. In some embodiments, planar surface 24 may have various surface configurations, for example, rough, arcuate, undulating, porous, semi-porous, dimpled, polished and/or textured. Head 20 has a diameter D2. Diameter D2 is greater than both diameters D1 and DD1 such that head 20 does not enter cavity 26 and maintains a substantially flush engagement with the outer surface of the superior facet.

A surface of head 20 defines a socket 21, as shown in FIG. 1. Socket 21 is configured for engagement with a surgical driver 100 to insert facet screw 12 into vertebrae V. In some embodiments, socket 21 has a hexalobe configuration. In some embodiments, socket 21 can include a circular, cruciform, phillips, square, polygonal, or star cross sectional configuration. In some embodiments, head 20 may be variously configured and dimensioned, for example, oval, oblong, square, rectangular, polygonal, irregular, uniform, non-uniform, offset, staggered, tapered, consistent or variable.

Figure 6:
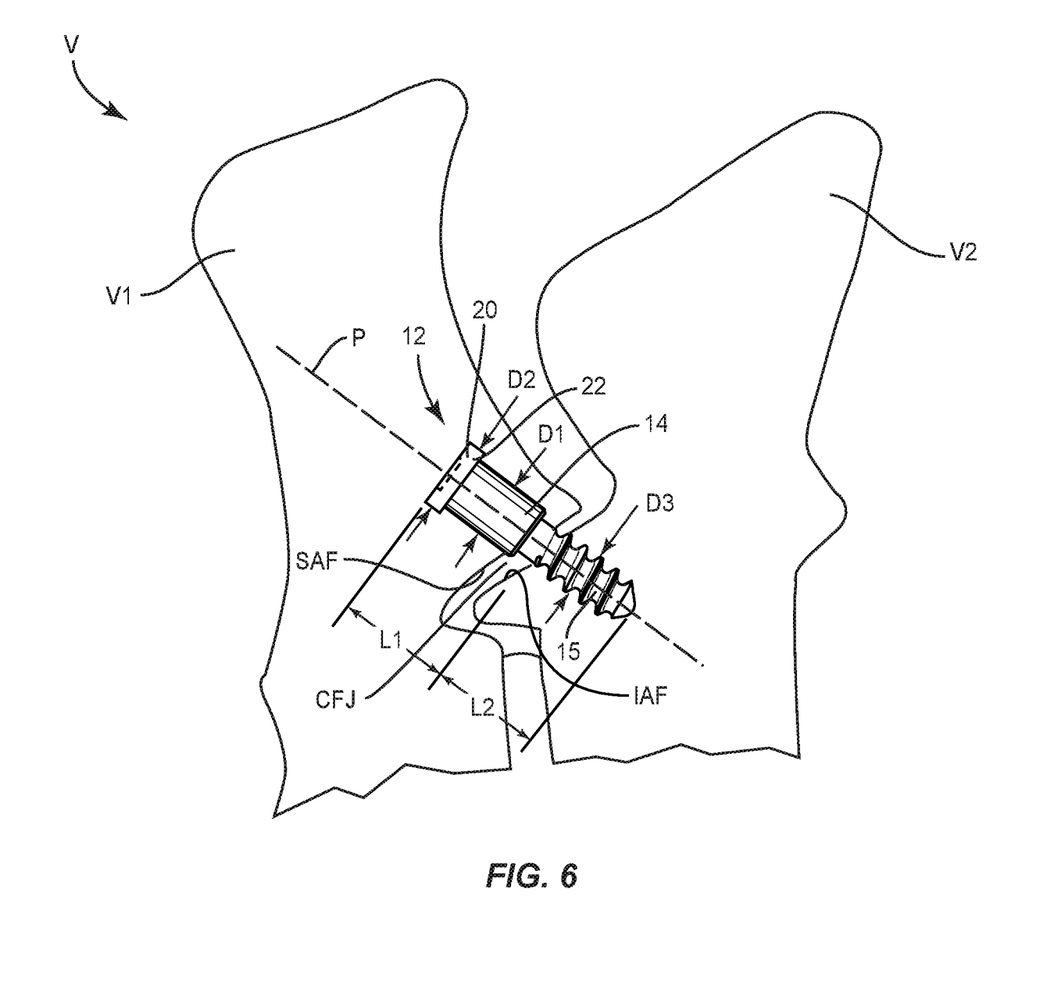
FIG. 6 is a side view of components of one embodiment of a spinal implant system in accordance with the principles of the present disclosure disposed with vertebrae.

Distal member 15 is configured for fixation with the inferior facet while proximal member 14 is disposed with the superior facet, such that the articular surfaces of the facets are drawn into engagement, as shown in FIGS. 6 and 7. Distal member 15 includes a shaft 31 configured for fixation with tissue surfaces of an opening, for example, cavity 38 formed within the inferior facet of V2. Shaft 31 includes an outer surface 32 that defines a thread form 34. Shaft 31 includes a non-threaded portion 35 disposed between thread form 34 and planar surface 24. Portion 35 is smooth. In some embodiments, thread form 34 may extend the entire length of shaft 31 or may extend only part of the length of shaft 31. In some embodiments, shaft 31 may include one thread form configuration or a plurality of different thread form configurations.

In some embodiments, the thread form configurations on outer surface 32 may include a single thread turn or a plurality of discrete threads. In some embodiments, other engaging structures may be located along outer surface 32, in place of or in addition to the thread form configurations discussed above, for example, a nail configuration, barbs, expanding elements, raised elements and/or spikes to facilitate engagement with tissue, for example, an inferior facet. Alternatively, in some embodiments, outer surface 32 may have various surface configurations, for example, rough, arcuate, undulating, porous, semi-porous, dimpled, polished and/or textured.

Shaft 31 has a diameter D3. Diameter D1 of body 16 is greater than diameter D3. Cavity 38 has a diameter DD2 and in some embodiments, cavity 38 is a pilot hole formed in tissue of the inferior facet. Diameter D3 is less than diameter DD1 of cavity 26 of the superior facet such that shaft 31 can pass through cavity 26 and into cavity 38 of the inferior facet and/or avoid tissue damage to the superior facet. Diameter D1 is greater than diameter DD2 to prevent proximal member 14 from disposal within cavity 38 such that proximal member 14 combined with distal member 15 draw the articular surfaces of the facets into engagement. Distal member 15 includes a length L2. Length L2 is greater than a length of cavity 38 such that shaft 31 is threaded with interior tissue surfaces of cavity 38 for fixation to ensure adequate facet screw 12 purchase. In some embodiments, length L1 is greater than length L2, length L1 is equal to length L2 or length L1 is less than length L2.

Distal member 15 includes a tip 36 to facilitate penetration of tissue, for example, the inferior facet. In some embodiments, tip 36 can be in a tapered and/or blunt configuration. In some embodiments, tip 36 can include other penetrating elements for example, a nail configuration, barbs, expanding elements, raised elements, ribs, and/or spikes to facilitate engagement of tip 36 with tissue.

Figure 2:
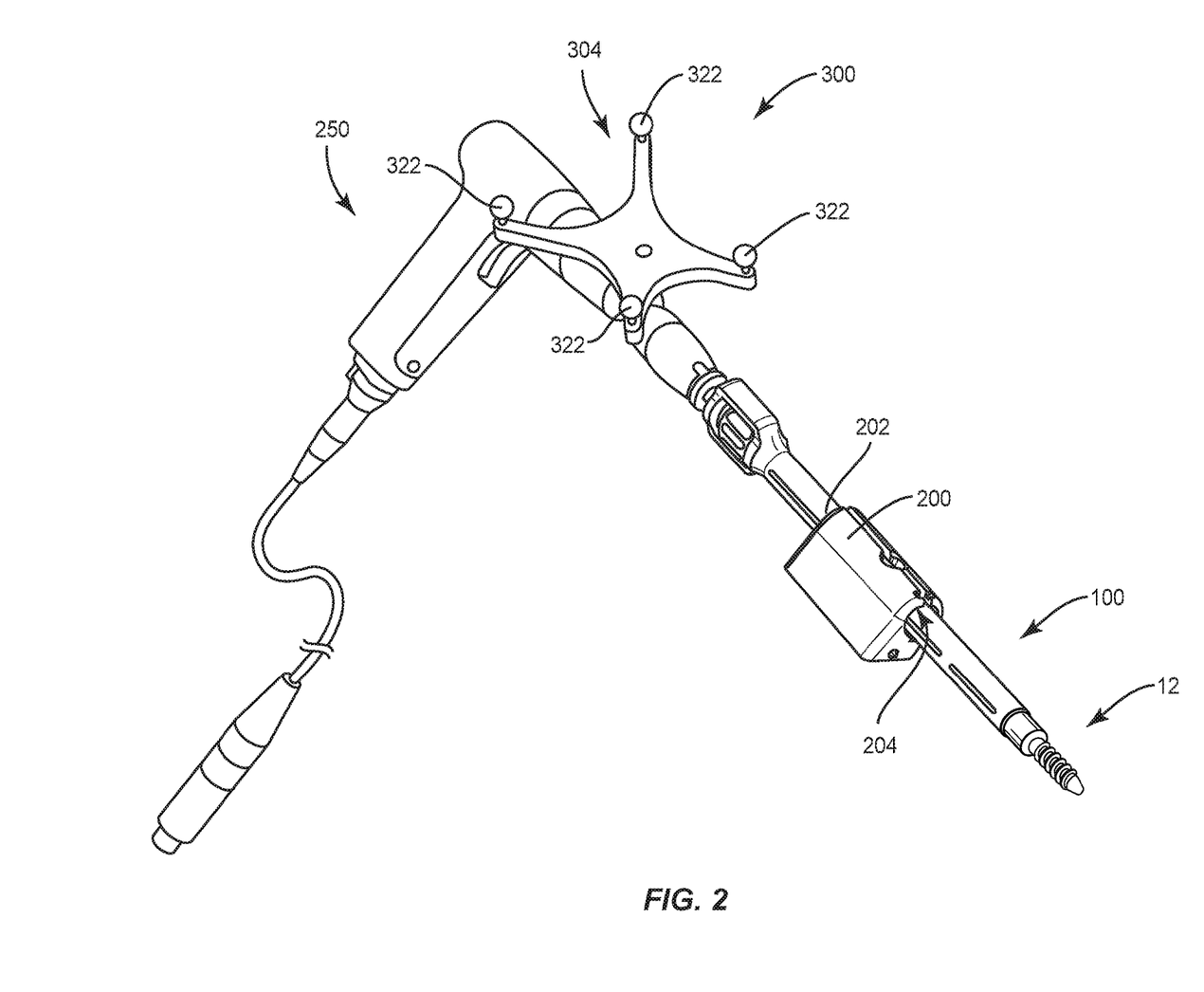
FIG. 2 is a perspective view of components of one embodiment of a spinal implant system in accordance with the principles of the present disclosure.
Figure 3:
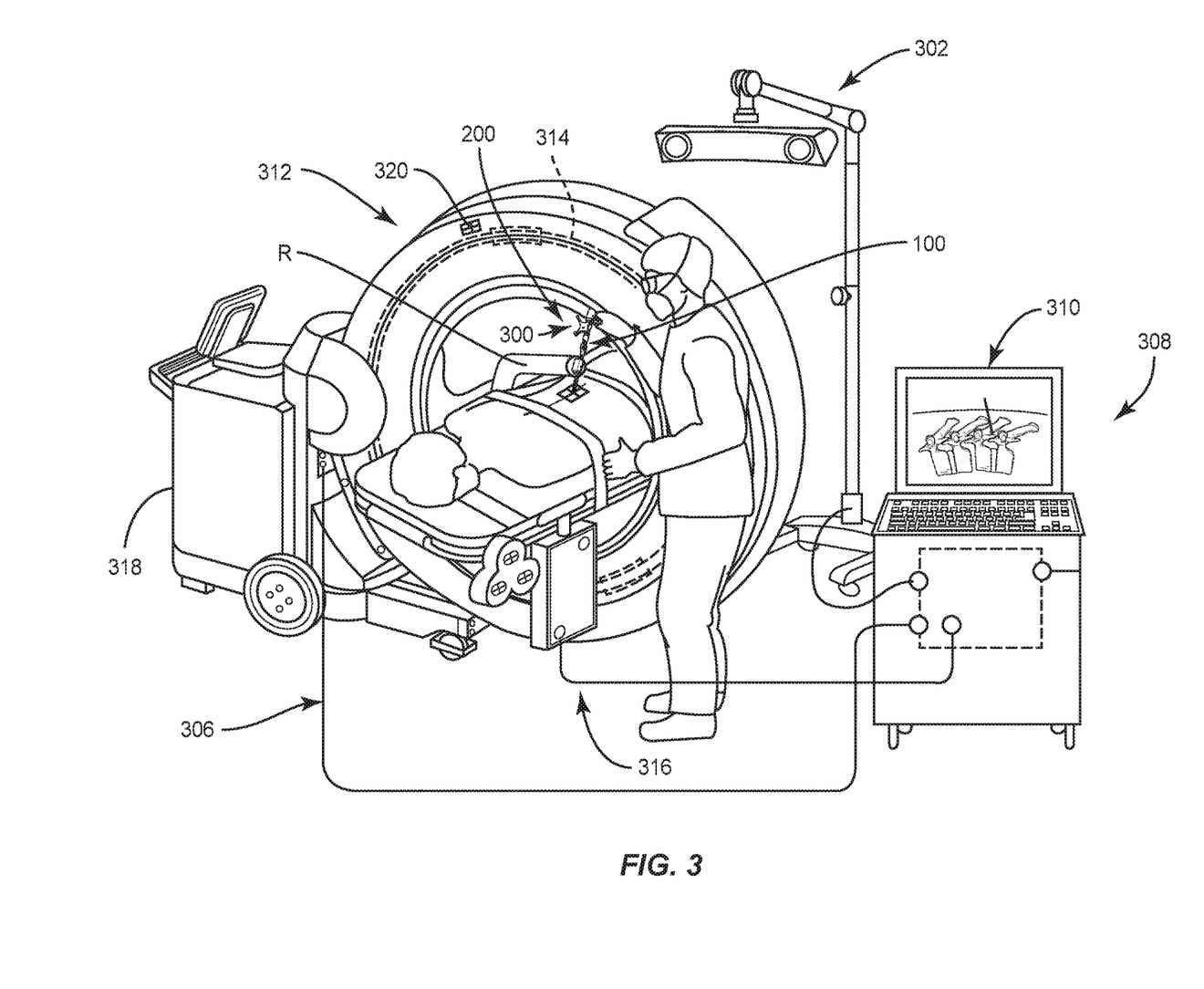
FIG. 3 is a perspective view of components of one embodiment of a spinal implant system in accordance with the principles of the present disclosure.

Driver 100 is engageable with socket 21. Driver 100 is configured for connection with a guide member, for example, an end effector 200 of a robotic arm R, as shown in FIGS. 2 and 3. Driver 100 is guided through end effector 200 for guide-wireless insertion of facet screw 12. End effector 200 includes an inner surface 202 that defines a cavity, for example, a channel 204, as shown in FIG. 2. Channel 204 is configured for passage of facet screw 12 and disposal of driver 100. Robotic arm R includes position sensors (not shown), similar to those referenced herein, which measure, sample, capture and/or identify positional data points of end effector 200 in three dimensional space for a guide-wireless insertion of facet screw(s) 12 with tissue. In some embodiments, the position sensors of robotic arm R are employed in connection with a surgical navigation system 306, as shown in FIG. 3, to measure, sample, capture and/or identify positional data points of end effector 200 in connection with surgical treatment, as described herein. The position sensors are mounted with robotic arm R and calibrated to measure positional data points of end effector 200 in three dimensional space, which are communicated to a computer 308.

In some embodiments, driver 100 includes a navigation component 300, as shown in FIG. 2. Driver 100 is configured for disposal adjacent a surgical site such that navigation component 300 is oriented relative to a sensor array 302 to facilitate communication between navigation component 300 and sensor array 302 during a surgical procedure, as described herein. Navigation component 300 is configured to generate a signal representative of a position of facet screw 12 relative to driver 100 and/or tissue, for example, the superior facet and the inferior facet. In some embodiments, driver 100 can include an image guide such as human readable visual indicia, human readable tactile indicia, human readable audible indicia, one or more components having markers for identification under x-ray, fluoroscopy, CT or other imaging techniques, at least one light emitting diode, a wireless component, a wired component, a near field communication component and/or one or more components that generate acoustic signals, magnetic signals, electromagnetic signals and/or radiologic signals. Navigation component 300 is directly connected to an actuator 250, for example, a powered drill, hand drill or other tool, as shown in FIG. 2. In some embodiments, navigation component 300 is connected with driver 100 via an integral connection, friction fit, pressure fit, interlocking engagement, mating engagement, dovetail connection, clips, barbs, tongue in groove, threaded, magnetic, key/keyslot and/or drill chuck.

Navigation component 300 includes an emitter array 304. Emitter array 304 is configured for generating a signal to sensor array 302 of surgical navigation system 306, as shown in FIG. 3 and described herein. In some embodiments, the signal generated by emitter array 304 represents a position of facet screw 12 relative to driver 100 and relative to tissue, for example, the superior facet and the inferior facet. In some embodiments, the signal generated by emitter array 304 represents a three dimensional position of facet screw 12 relative to the superior facet and the inferior facet.

In some embodiments, sensor array 302 receives signals from emitter array 304 to provide a three-dimensional spatial position and/or a trajectory of facet screw 12 relative to driver 100 and/or the superior facet and the inferior facet. Emitter array 304 communicates with a processor of computer 308 of surgical navigation system 306 to generate data for display of an image on a monitor 310, as described herein. In some embodiments, sensor array 302 receives signals from emitter array 304 to provide a visual representation of a position of facet screw 12 relative to driver 100 and/or the superior facet and the inferior facet. See, for example, similar surgical navigation components and their use as described in U.S. Pat. Nos. 6,021,343, 6,725,080, 6,796,988, the entire contents of each of these references being incorporated by reference herein.

Surgical navigation system 306 is configured for acquiring and displaying medical imaging, for example, x-ray images appropriate for a given surgical procedure. In some embodiments, pre-acquired images of a patient are collected. In some embodiments, surgical navigation system 306 can include an O-arm® imaging device 312 sold by Medtronic Navigation, Inc. having a place of business in Louisville, Colo., USA. Imaging device 312 may have a generally annular gantry housing that encloses an image capturing portion 314.

In some embodiments, image capturing portion 314 may include an x-ray source or emission portion and an x-ray receiving or image receiving portion located generally or as practically possible 180 degrees from each other and mounted on a rotor (not shown) relative to a track of image capturing portion 314. Image capturing portion 314 can be operable to rotate 360 degrees during image acquisition. Image capturing portion 314 may rotate around a central point or axis, allowing image data of the patient to be acquired from multiple directions or in multiple planes. Surgical navigation system 306 can include those disclosed in U.S. Pat. Nos. 8,842,893, 7,188,998; 7,108,421; 7,106,825; 7,001,045; and 6,940,941; the entire contents of each of these references being incorporated by reference herein.

In some embodiments, surgical navigation system 306 can include C-arm fluoroscopic imaging systems, which can generate three-dimensional views of a patient. The position of image capturing portion 314 can be precisely known relative to any other portion of an imaging device of navigation system 306. In some embodiments, a precise knowledge of the position of image capturing portion 314 can be used in conjunction with a tracking system 316 to determine the position of image capturing portion 314 and the image data relative to the patient.

Tracking system 316 can include various portions that are associated or included with surgical navigation system 306. In some embodiments, tracking system 316 can also include a plurality of types of tracking systems, for example, an optical tracking system that includes an optical localizer, for example, sensor array 302 and/or an EM tracking system that can include an EM localizer. Various tracking devices can be tracked with tracking system 316 and the information can be used by surgical navigation system 306 to allow for a display of a position of an item, for example, a patient tracking device, an imaging device tracking device 320, and an instrument tracking device, for example, emitter array 304, to allow selected portions to be tracked relative to one another with the appropriate tracking system.

In some embodiments, the EM tracking system can include the STEALTHSTATION® AXIEM™ Navigation System, sold by Medtronic Navigation, Inc. having a place of business in Louisville, Colo. Exemplary tracking systems are also disclosed in U.S. Pat. Nos. 8,057,407, 5,913,820, 5,592,939, the entire contents of each of these references being incorporated by reference herein.

Fluoroscopic images taken are transmitted to a computer 318 where they may be forwarded to computer 308. Image transfer may be performed over a standard video connection or a digital link including wired and wireless. Computer 308 provides the ability to display, via monitor 310, as well as save, digitally manipulate, or print a hard copy of the received images. In some embodiments, images may also be displayed to the surgeon through a heads-up display.

In some embodiments, surgical navigation system 306 provides for real-time tracking of the position of facet screw 12 relative to driver 100 and/or tissue for example, the superior facet and the inferior facet can be tracked. Sensor array 302 is located in such a manner to provide a clear line of sight with emitter array 304, as described herein. In some embodiments, fiducial markers 322 of emitter array 304 communicate with sensor array 302 via infrared technology. Sensor array 302 is coupled to computer 308, which may be programmed with software modules that analyze signals transmitted by sensor array 302 to determine the position of each object in a detector space.

In assembly, operation and use, spinal implant system 10, similar to the systems and methods described herein, is employed with a surgical procedure, for example, a treatment of an applicable condition or injury of an affected section of a spinal column and adjacent areas within a body. In some embodiments, spinal implant system 10 is employed with a surgical procedure for treatment of a cervical facet joint (CFJ) of a patient, as shown in FIGS. 4-7. In some embodiments, one or all of the components of spinal implant system 10 can be delivered or utilized as a pre-assembled device or can be assembled in situ. Spinal implant system 10 may be completely or partially revised, removed or replaced.

In use, to treat a CFJ of a patient, a medical practitioner obtains access to a surgical site including vertebrae V1 and V2 in any appropriate manner, such as through incision and retraction of tissues. In some embodiments, spinal implant system 10 can be used in any existing surgical method or technique including open surgery, mini-open surgery, minimally invasive surgery and percutaneous surgical implantation, whereby the facet joint is accessed through a mini-incision, or a sleeve that provides a protected passageway to the area. Once access to the surgical site is obtained, the selected surgical procedure can be performed for treating the spine disorder.

Figure 4:
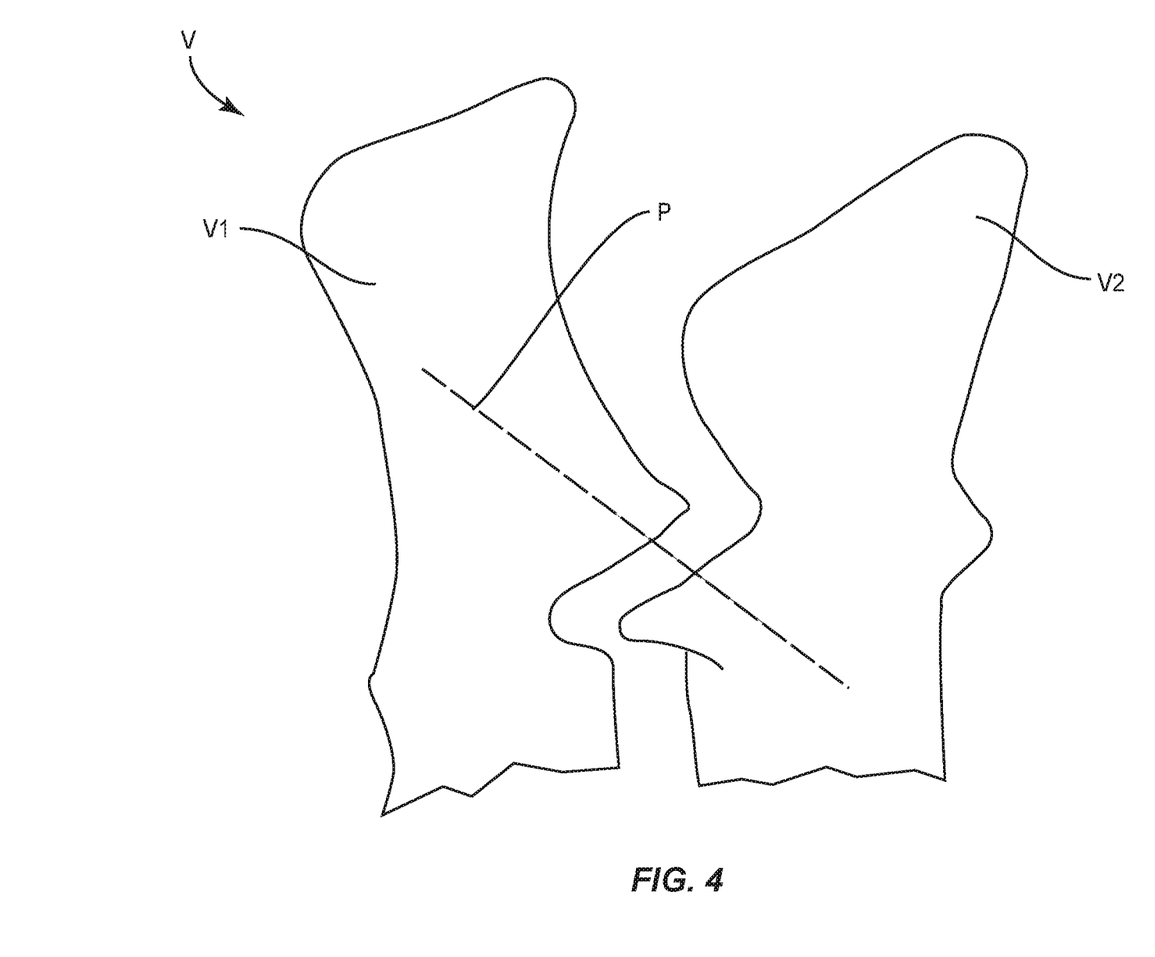
FIG. 4 is a side view of a surgical pathway for components of one embodiment of a spinal implant system and vertebrae in accordance with the principles of the present disclosure.

An incision is made in the body of a patient and a cutting instrument (not shown) creates a selected surgical pathway P, as shown in FIG. 4, including a facet joint, for example, a CFJ including at least a portion of a facet for example, the superior articular facet (SAF) of vertebra V1 and at least a portion of an adjacent facet, for example, the inferior articular facet (IAF) of vertebra V2 for implantation of facet screw 12, described herein. A speculum (not shown) can be employed to assist in creating the surgical pathway P. Tissue can be spaced with a retractor (not shown). A preparation instrument (not shown) can be employed to prepare tissue surfaces of vertebrae V, as well as for aspiration and irrigation of a surgical region.

Figure 5:
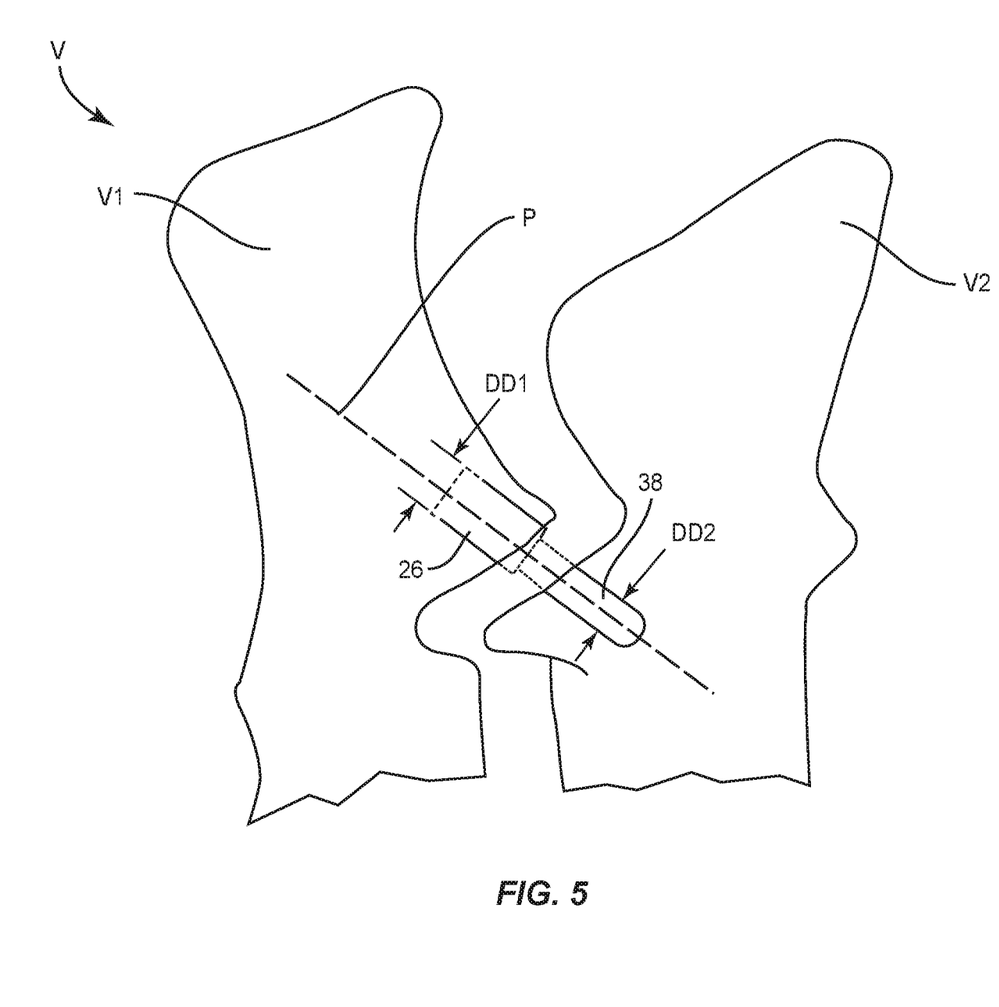
FIG. 5 is a side view of a surgical pathway for components of one embodiment of a spinal implant system and vertebrae in accordance with the principles of the present disclosure.

An opening, for example, cavity 26 is created in the SAF of vertebra V1 along the surgical pathway P from a posterior approach to the vertebrae. An opening, for example, cavity 38 is created in the IAF of vertebra V2 along the surgical pathway P from a posterior approach to vertebrae V1, V2. Cavities 26 and 38 include pilot holes, for example, stepped pilot holes that are formed with a drill (not shown) in the selected areas. Cavity 26 includes a diameter DD1 and cavity 38 includes a diameter DD2, as shown in FIG. 5. Diameter DD1 is greater than DD2 such that proximal member 14 of screw 12 is engageable with cavity 26 and distal member 15 of facet screw 12 is engageable with cavity 38.

In some embodiments, for anterior cervical disc fixation with facet screw 12, the patient is placed in a lateral position and the surgical pathway P can be oriented from a lateral anterior approach. Cavities 26, 38 can then be created in V1 and V2 in the lateral position.

Driver 100 is engaged with socket 21 of facet screw 12, as shown in FIG. 2. Driver 100 is oriented for disposal with end effector 200 of robotic arm R. The assembly of driver 100/facet screw 12 is disposed with channel 204 for delivery/implantation of facet screw 12 with cavity 26 of V1 and cavity 38 of V2 to draw articular surfaces of the facets into engagement employing robotic arm R and/or surgical navigation system 306. Actuator 250 is connected with driver 100, as described herein, and driver 100 is utilized to drive, torque, insert or otherwise connect facet screw 12 with both V1 and V2, as shown in FIG. 7. For example, facet screw 12 is inserted into cavity 26 formed within the SAF of V1 and surface 18 of body 16 of proximal member 14 slidably engages tissue surfaces of cavity 26. Body 16 translates into the CFJ but does not enter into V2. As proximal member 14 engages with tissue surfaces of cavity 26 and is inserted into the CFJ, shaft 31 of distal member 15 is inserted into cavity 38 formed within the IAF of V2. As shaft 31 is inserted into cavity 38, shaft 31 is rotated and thread form 34 fixedly engages with the interior tissue surfaces of cavity 38. During shaft 31 fixation with the interior tissue surfaces of cavity 38, planar surface 24 of circumferential flange 22 of head 20 engages with outer surface (S) of the superior facet (SF) in a substantially flush engagement which draws the SAF and the IAF together. As planar surface 24 engages with S of the SF, shaft 31 is fixed with IF for compression capability to draw articular surfaces of the facets into engagement, as shown in FIGS. 6 and 7. In some embodiments, driver 100 is manipulated to deliver one or more facet screws 12 to a surgical site including the CFJ.

Sensor array 302 receives signals from navigation component 300 to provide a three-dimensional spatial position and/or a trajectory of the assembly of driver 100/facet screw 12, which may be disposed with end effector 200, relative to the CFJ and/or components of spinal implant system 10 for display on monitor 310. Driver 100 is manipulated to disengage with and translate away from facet screw 12.

Upon completion of a procedure, the surgical instruments, assemblies and non-implanted components of spinal implant system 10 are removed and the incision(s) are closed. One or more of the components of spinal implant system 10 can be made of radiolucent materials such as polymers. Radiomarkers may be included for identification under x-ray, fluoroscopy, CT or other imaging techniques. In some embodiments, spinal implant system 10 may include one or a plurality of spinal rods, plates, connectors and/or bone fasteners for use with a single vertebral level or a plurality of vertebral levels.

In some embodiments, one or more spinal implants of spinal implant system 10, may be engaged with tissue in various orientations, for example, series, parallel, offset, staggered and/or alternate vertebral levels. In some embodiments, the spinal implant of spinal implant system 10 may comprise multi-axial screws, sagittal adjusting screws, pedicle screws, mono-axial screws, uni-planar screws, facet screws, fixed screws, tissue penetrating screws, conventional screws, expanding screws, wedges, anchors, buttons, clips, snaps, friction fittings, compressive fittings, expanding rivets, staples, nails, adhesives, posts, fixation plates and/or posts.

In some embodiments, spinal implant system 10 includes an agent, which may be disposed, packed, coated or layered within, on or about the components and/or surfaces of spinal implant system 10. In some embodiments, the agent may include bone growth promoting material, for example, bone graft to enhance fixation of the components and/or surfaces of spinal implant system 10 with vertebrae. In some embodiments, the agent may include one or a plurality of therapeutic agents and/or pharmacological agents for release, including sustained release, to treat, for example, pain, inflammation and degeneration.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A spinal implant comprising:
   a proximal member including a body having a first diameter and a head having a second diameter, the body including an outer surface disposed for non-fixation with a superior facet of a vertebra and the second diameter being greater than the first diameter;
   a distal member having a third diameter and being configured for fixation with an inferior facet of an adjacent vertebra, wherein the proximal member is configured for disposal with an opening of the superior facet, the proximal member having a length greater than a length of the opening and the distal member is configured for disposal with an opening of the inferior facet, the distal member having a length greater than a length of the opening.

2. A spinal implant as recited in claim 1, wherein the distal member engages the inferior facet and the head engages the superior facet such that articular surfaces of the facets are drawn into engagement.

3. A spinal implant as recited in claim 1, wherein the head includes a circumferential flange extending from the outer surface and being engageable with the superior facet.

4. A spinal implant as recited in claim 3, wherein the flange includes a planar surface disposed in substantially flush engagement with the superior facet.

5. A spinal implant as recited in claim 1, wherein the outer surface includes a uniform, even surface configuration.

6. A spinal implant as recited in claim 1, wherein the non-fixation of the outer surface includes a non-penetrating, slidable engagement with the superior facet.

7. A spinal implant as recited in claim 1, wherein the first diameter is greater than the third diameter.

8. A spinal implant as recited in claim 1, wherein the proximal member is engageable with a surgical driver connected to a guide member having an end effector of a robotic arm.

9. A spinal implant as recited in claim 8, wherein the surgical driver includes a surgical navigation component.

10. A spinal implant as recited in claim 9, wherein the surgical navigation component communicates with a tracking device including a sensor that receives a signal and communicates with a processor to generate data for display of an image from a monitor, the image representing position of the spinal implant relative to the facets.

11. A method for treating a spine, the method comprising the steps of:
    selecting a pathway that includes a facet joint including at least a portion of a facet of a first vertebra and at least a portion of a facet of a second vertebra;
    creating an opening in the facets along the pathway from a posterior approach to the vertebrae, the opening including a first diameter cavity of the facet of the first vertebra and a second diameter cavity of the facet of the second vertebra, the first diameter being greater than the second diameter; and
    delivering an implant along the pathway such that the implant is disposed in the first diameter cavity and the second diameter cavity to draw articular surfaces of the facets into engagement.

12. A method as recited in claim 11, wherein the first diameter cavity includes a pilot hole formed in the superior articular facet and the second diameter cavity includes a pilot hole formed in the inferior articular facet.

13. A method as recited in claim 11, wherein the implant includes a proximal member having a body with a first diameter and a head having a second diameter, and a distal member configured for fixation with tissue.

14. A method as recited in claim 11, wherein the distal member engages an inferior facet of the second vertebra and the head engages a superior facet of the first vertebra such that the articular surfaces of the facets are drawn into engagement.

15. A method as recited in claim 11, wherein the implant includes a proximal member having a circumferential flange with a diameter greater than the first diameter, the flange being engageable with a superior facet of the first vertebra.

16. A method as recited in claim 11, wherein the implant includes a proximal member having a body configured for disposal with the first diameter cavity, the body including an outer surface configured for a non-penetrating, slidable engagement with the facet of the first vertebra.

17. A method as recited in claim 11, wherein the step of delivering includes engaging a surgically navigated driver with the implant.

18. A method for treating a spine, the method comprising the steps of:
    identifying a facet joint including at least a portion of a superior articular facet of a vertebra and at least a portion of an inferior articular facet of an adjacent vertebra;
    determining a selected pathway that includes the facet joint;
    creating an opening in the facets along the selected pathway from a posterior approach to the vertebrae, the opening including a first diameter cavity of the superior articular facet and a second diameter cavity of the inferior articular facet, the first diameter being greater than the second diameter; and
    delivering an implant along the selected pathway via surgical navigation, the implant including a proximal member having a body with a first diameter and a head with a second diameter that is greater than the first diameter and a distal member configured for fixation with tissue such that the proximal member is disposed in the first diameter cavity and the distal member is disposed in the second diameter cavity to draw surfaces of the articular facets into engagement.

* * * * *